United States Patent [19]

Blackhurst

[11] Patent Number: 4,683,336

[45] Date of Patent: Jul. 28, 1987

[54] PREPARATION OF AMINES

[75] Inventor: Clarence W. Blackhurst, Worthington, Ohio 43085

[73] Assignee: Sherex Chemical Company Inc., Dublin, Ohio

[21] Appl. No.: 808,693

[22] Filed: Dec. 13, 1985

[51] Int. Cl.$^4$ .............................................. C07C 85/06
[52] U.S. Cl. .................................... 564/480; 564/473
[58] Field of Search ................................ 564/473, 480

[56] References Cited

U.S. PATENT DOCUMENTS 4,014,933 3/1977 Boettger et al. ................ 564/480 X
4,210,605 7/1980 Hoshino et al. ...................... 564/473
4,404,403 9/1983 Swift et al. ........................... 560/473
4,404,404 9/1983 Swift et al. ........................... 560/473
4,409,399 10/1983 Swift et al. .......................... 560/473

Primary Examiner—Paul F. Shaver
Attorney, Agent, or Firm—Pollock, Vande Sande & Priddy

[57] ABSTRACT

Amines are produced by reacting an aliphatic alcohol and/or an aliphatic aldehyde with an aminating agent in the presence of a catalyst containing copper carbonate and nickel carbonate and/or cobalt carbonate.

24 Claims, No Drawings

PREPARATION OF AMINES

TECHNICAL FIELD

The present invention is concerned with a process for producing amines and particularly for producing aliphatic amines. The process of the present invention is concerned with reacting an aliphatic alcohol and/or an aliphatic aldehyde with an aminating agent such as ammonia, a primary amine, or a secondary amine. The present invention is particularly concerned with a liquid phase reaction.

BACKGROUND ART

The preparation of amines by reacting aliphatic alcohols and aliphatic aldehydes with an aminating agent in the liquid phase is well-known. In addition, the use of various copper-containing and/or nickel-containing materials as catalysts for such reaction is also known. For instance, both supported and unsupported copper-containing and/or nickel-containing catalysts have been suggested for such purpose. For example, it has been suggested to carry out such processes under particular conditions employing an unsupported catalyst containing copper oxide or copper hydroxide in combination with nickel oxide or nickel hydroxide. Also, copper has been suggested in the form of cupric oxide on a refractory support or as a copper chromite catalyst.

For instance, copper oxide supported on alumina or silica gel has been suggested for such purpose. Also, copper barium chromite has been suggested as a catalyst for preparing aliphatic amines. Further suggestions of catalysts include nickel-copper-chromia catalysts or nickel, copper catalyst in conjunction with iron, zinc, zirconium, or mixtures thereof.

SUMMARY OF THE INVENTION

It has been found, in accordance with the present invention, that relatively high yields of amine are obtainable by carrying out a liquid phase reaction of an aliphatic alcohol or aliphatic aldehyde with ammonia, a primary amine, or a secondary amine employing as catalysts copper carbonate and a carbonate of nickel and/or cobalt. In addition, it has been found, in accordance with the present invention, that the process can be carried out under relatively moderate temperature conditions and low pressures. A further advantage of the present invention is that the catalysts can be readily separated from the reaction product by filtration.

Accordingly, the present invention is directed to a process for producing amines, which process includes reacting an aliphatic alcohol and/or aliphatic aldehyde with an aminating agent being ammonia, a primary amine, a secondary amine, or mixtures thereof. The reaction is carried out in the liquid phase and in the presence of a catalytic amount of an unsupported catalyst comprising copper carbonate and a carbonate of nickel and/or cobalt. The term "liquid phase" is intended to mean a process wherein the alcohol and/or the aldehyde is in the liquid phase and the aminating agent (e.g., ammonia, primary amine, and secondary amine) are in either the liquid or gaseous phase under the conditions of the reaction.

BEST AND VARIOUS MODES FOR CARRYING OUT INVENTION

The process of the present invention is carried out in the presence of a catalytic amount of an unsupported catalyst which contains copper carbonate and nickel carbonate or cobalt carbonate or mixtures of nickel carbonate and cobalt carbonate. The copper-to-nickel and/or cobalt weight ratio in the catalyst is generally from about 0.5:1 to about 5:1 and preferably from about 1:1 to about 3:1.

The catalyst can be either a physical mixture of the copper carbonate and nickel carbonate and/or cobalt carbonate or a composite of the copper carbonate and nickel carbonate and/or cobalt carbonate.

The alcohols employed in the present invention are preferably primary alcohols and can be defined by the formula $RCH_2OH$. The aldehydes which can be employed in accordance with the present invention can be defined by the formula RCHO. In the above formulas R is a linear or branched, saturated or unsaturated aliphatic group having from about 7 to about 23 carbon atoms and preferably from 7 to 17 carbon atoms.

Examples of aliphatic alcohols that can be employed in accordance with the present invention include 1-octanol, 1-decanol, 1-dodecanol, 1-tetradecanol, 1-hexadecanol, 1-octadecanol, 2-ethyl-1-hexanol, oleyl alcohol, and 1-nonanol. Of course, mixtures of alcohols can be employed if desired.

Examples of some aliphatic aldehydes include 1-octanal, 1-decanal, 1-dodecanal, 1-tetradecanal, 1-hexadecanal, 1-octadecanal, 2-ethyl hexanal, oleyl aldehyde, and 1-nonanal. Of course, mixtures of aldehydes and/or mixtures of aldehydes with alcohols can be employed if desired.

The ammonia or amines employed in accordance with the present invention can be defined by the following formula: $HNR_1R_2$ wherein $R_1$ and $R_2$, individually, are hydrogen or a linear or branched, saturated or unsaturated aliphatic group having from 1 to 24 carbon atoms and preferably from 1 to 18 carbon atoms. $R_1$ and $R_2$ can also be interconnected and together with the nitrogen atom to which such are interconnected form a heterocyclic ring.

Examples of some primary amines are monomethylamine, monoethylamine, dodecylamine, hexadecylamine, 2-ethylhexylamine, and cyclohexylamine.

Examples of secondary amines are dimethylamine, diethylamine, dodecylmethylamine, dioctylamine, piperidine, and morpholine.

Of course, mixtures of amines and mixtures of amines with ammonia can be employed if desired.

The relative amounts of the alcohol and/or aldehyde in comparison to the amine and/or ammonia can vary greatly. In the preferred aspects of the present invention, the ammonia or amine is usually employed in excess of the alcohol and/or aldehyde such as up to about 30% excess and most preferably in about 10% excess of the stoichiometric amount. Less preferable approximately stoichiometric amounts of the reactants are employed.

Examples of some amines prepared in accordance with the present invention are dodecyldimethylamine, N-dodecylpiperidine, dodecylmonomethylamine, didodecylmethylamine, didodecylamine, 2-ethylhexyldimethylamine, tristearylamine, oleyldimethylamine, tetradecyldimethylamine, hexadecyldimethylamine, and octadecyldimethylamine.

The process of the present invention can be carried out by merely bringing together the reactants and catalysts discussed hereinabove with adequate mixing or stirring at a temperature of about 170° C. to about 250°

C. and preferably about 195° C. to about 230° C. The pressure employed is usually about 1 atmosphere. However, greater or lesser pressure can be employed if desired. It is preferred, however, that atmosphere pressure be employed.

The amount of catalyst employed is usually from about 0.5 to about 10 grams and preferably about 1 to about 1.4 grams per hundred grams of alcohol and/or aldehyde employed. In the preferred aspects of the present invention, during the time the reaction mass is brought to the temperature of reaction, a hydrogen sparge of about 0.1 to about 2 standard cubic feet per hour per 100 grams of alcohol and/or aldehyde is employed. This provides for an increased reaction rate. The heating up to the reaction temperature usually takes about 15 to about 180 minutes.

In a typical procedure to carry out the present invention, the liquid alcohol and/or liquid aldehyde is charged to a stirred reaction vessel along with the catalyst composition. After this, the reaction vessel is purged with a gas such as nitrogen or hydrogen. Then, as the reaction vessel is heated to a reaction temperature, the hydrogen gas is introduced into and through the liquid phase. When the desired reaction temperature has been reached, hydrogen and the amine and/or ammonia are passed through the reaction mixture together as one stream and/or as separate feed streams.

The off-gases comprising hydrogen, unreacted amine, water of reaction, and traces of unreacted alcohol or aldehyde and traces of product amine are continuously removed from the reaction zone. The off-gases can be cooled to separate water, and an organic phase which can be returned to the reactor.

If desired, the off-gases can also be recycled to the reaction zone. This can be continued until the conversion of the alcohol and/or aldehyde is substantially completed.

In order to remove the catalyst, the reaction product can be subjected to a filtration. If desired, the catalyst can be recycled.

The product amine, in many instances, can be further purified, if desired, by distillation such as vacuum distillation. The distillation can be carried out before or after the removal of the catalyst.

The following non-limiting examples are presented to further illustrate the present invention.

EXAMPLE 1

To a two liter stirred autoclave are charged about 550 grams of tallow alcohol (about 2.06 moles), about 4.4 grams of commercial copper carbonate, and about 2.2 grams of commercial nickel carbonate. A hydrogen flow is started through the vented reactor below the alcohol surface at a rate of about 0.69 standard cubic feet per hour (scfh). The reactor is then heated to about 210° C. over about one hour. Hydrogen flow is increased to about 1.38 scfh while a dimethylamine (DMA) vapor feed is started below the reaction surface at about 0.45 scfh. After about four hours under these conditions about 102 grams (2.27 moles, or 1.1 mole/mole of alcohol) of dimethylamine has been fed. A sample is removed for analysis and conditions are continued for another hour until the DMA/alcohol mole ratio has reached 1.3/1. The dimethylamine flow is stopped and H$_2$ flow is cut in half during cooling. The product is removed and filtered at 90° F. on a Buckner funnel. Analysis of the four hour sample shows the composition to be 94.8% dimethylalkylamine (DMAA), 3.7% alcohol, and 1.2% ester. Composition after five hours is 98.8% DMAA and 1.2% ester. Product color, after filtration is <1 Gardner, off shade green. The crude product is distilled under reduced pressure yielding a distillate (93.7% of feed) composed of 100% DMAA.

EXAMPLE 2

Stearyl alcohol is converted to dimethylstearylamine using the same equipment and conditions as described in Example 1. The product analysis after four hours run is 94.3% DMAA, 1.8% ROH, and 1.8% ester. After five hours the product is 98.1 DMAA, 0% alcohol, and 1.9% ester. The distilled product (94.7% of feed) is 100% dimethylstearylamine.

EXAMPLE 3

Oleyl alcohol is converted to dimethyloleylamine as described in Example 1. Product analysis at four hours is 94.8% DMAA, 2.8% alcohol, and 1.2% ester. After five hours the analysis is 97.4% dimethyloleylamine, 0% alcohol, and 1.2% ester.

EXAMPLE 4

About 550 grams of tallow alcohol (about 2.06 moles), about 4.4 grams of copper carbonate, and about 2.2 grams of nickel carbonate are charged to the 2-1 stirred autoclave (vent open). A hydrogen sparge of about 0.5 scfh is started and continued while heating the reaction mass to about 210° C. (about one hour). The hydrogen sparge is increased to 1.0 scfh and a monomethylamine (MMA) vapor stream is fed simultaneously, below the surface, at a rate of about 0.2 grams per minute (0.32 scfh). After about three hours, when the alcohol content is about 2.5% and methylalkyl secondary amine is about 5.3%, MMA feed is stopped, but hydrogen is continued for about three more hours. The product is cooled to about 90° F. and filtered on a Buckner funnel. The crude product has a Gardner 3 color and contains 92.1% dialkylmethylamine (DAMA), 4.8% dialkyl secondary amine, 0.9% dimethylalkylamine, and 1.6% alcohol plus methylalkyl secondary amine.

EXAMPLE 5

About 550 grams of oleyl alcohol, about 3.83 grams of commercial copper carbonate, and about 1.6 grams of cobalt carbonate (2/1 Cu/Co) are charged to a one-liter resin flask fitted with a stirrer, thermometer, Fredrich condenser, Barret water trap, and a ¼" OD sparge tube. A hydrogen stream is sparged at 2.0 scfh and maintained during heating over about one hour to about 210° C. A DMA stream was started at about 0.71 scfh. After about five hours the reaction is cooled to room temperature and filtered. The crude product is composed of 89.6% DMAA, 4% DAMA, 1.8% alcohol, and 0.8% ester.

EXAMPLE 6

The reaction described in Example 5 is repeated, except that about 1.48 grams of nickel hydroxide is substituted for the cobalt carbonate. Product analysis is 87.8% DMAA, 1.8% DAMA, 6.8% alcohol, and 0.2% ester.

EXAMPLE 7

The reaction described in Example 5 is repeated using only about 3.83 grams of commercial copper carbonate as catalyst. The product contains 73.2% tertiary amine as determined by HCl titration.

Having thus described our invention, what I claim as new and desire to secure by Letters Patent is:

1. A process for producing amines which comprises reacting an aliphatic alcohol or an aliphatic aldehyde with an aminating agent selected from the group of ammonia, primary amine, and secondary amine in the liquid phase in the presence of a catalytic amount of an unsupported catalyst comprising copper carbonate and a carbonate of a metal selected from the group of nickel, cobalt, and mixtures thereof.

2. The process of claim 1 wherein said catalyst comprises nickel carbonate.

3. The process of claim 1 wherein said catalyst comprises cobalt carbonate.

4. The process of claim 1 wherein the weight ratio of copper to nickel or cobalt or both is about 0.5:1 to about 5:1.

5. The process of claim 1 wherein the weight ratio of copper to nickel or cobalt or both is about 1:1 to about 3:1.

6. The process of claim 1 wherein said alcohol is a primary alcohol.

7. The process of claim 1 wherein said alcohol or said aldehyde contains about 8 to about 24 carbon atoms.

8. The process of claim 1 wherein said alcohol or said aldehyde contains about 8 to about 18 carbon atoms.

9. The process of claim 1 wherein approximately stoichiometric amounts of the reactants are employed.

10. The process of claim 1 wherein the ammonia or amine is employed in excess of the stoichiometric amount of the alcohol or aldehyde or both.

11. The process of claim 10 wherein said excess is up to about 30%.

12. The process of claim 10 wherein said excess is up to about 10%.

13. The process of claim 1 wherein the temperature of the reaction is about 170° C. to about 250° C.

14. The process of claim 1 wherein the temperature of the reaction is about 195° C. to about 230° C.

15. The process of claim 1 wherein the catalyst is employed in amounts of about 0.5 to about 10 grams per 100 grams of alcohol or aldehyde or both.

16. The process of claim 1 wherein the catalyst is employed in amounts of about 1 to about 1.4 grams per 100 grams of alcohol or aldehyde or both.

17. The process of claim 1 which further comprises a hydrogen sparge.

18. The process of claim 17 wherein said hydrogen sparge is about 0.1 to about 2 standard cubic feet per hour per 100 grams of alcohol or aldehyde or both.

19. The process of claim 1 wherein tallow alcohol is employed as a reactant.

20. The process of claim 1 wherein stearyl alcohol is employed as a reactant.

21. The process of claim 1 wherein oleyl alcohol is employed as a reactant.

22. The process of claim 1 wherein the amine employed is dimethylamine or monomethylamine.

23. The process of claim 1 wherein said unsupported catalyst is separated from the amines by filtration.

24. The process of claim 1 wherein the pressure is about 1 atmosphere.

* * * * *